United States Patent [19]

Trostmann et al.

[11] Patent Number: 4,855,489

[45] Date of Patent: Aug. 8, 1989

[54] 2-ACYLOXYPROPYLAMINO DERIVATIVES, PROCESSES FOR THE PREPARATION THEREOF, AND PHARMACEUTICAL COMPOSITIONS CONTAINING THEM

[75] Inventors: Uwe Trostmann, Mühlenweg; Christoph Schächtele, Spechtweg; Karl Mannhardt, Graf Toerring; Claus Rudolph, Gewerbestr; Marmé Dieter, Kaschnitzweg, all of Fed. Rep. of Germany

[73] Assignee: Goedecke Aktiengesellschaft, Berlin, Fed. Rep. of Germany

[21] Appl. No.: 73,926

[22] Filed: Jul. 15, 1987

[30] Foreign Application Priority Data

Jul. 30, 1986 [DE] Fed. Rep. of Germany ....... 3625738

[51] Int. Cl.$^4$ .......................................... C07C 67/02

[52] U.S. Cl. .................................... 560/250; 560/252; 560/253; 544/399

[58] Field of Search ...................... 560/250, 252, 253; 514/315, 255, 546; 544/399

[56] References Cited

PUBLICATIONS

Mamedov, Shamkhal, Chem. Abstracts, 66:54966a, (1966).
Babulova et al., Chemical Abstracts, 54:4895a, 1960.

*Primary Examiner*—Paul J. Killos
*Attorney, Agent, or Firm*—Elizabeth M. Anderson

[57] ABSTRACT

The present invention covers a novel series of 2-acyloxypropylamine derivatives, processes for preparing them, compositions containing them, and methods for using them. The compounds are active in the inhibition of protein kinase C and thrombocyto aggregation stimulated by diacylglycerols.

21 Claims, No Drawings

2-ACYLOXYPROPYLAMINO DERIVATIVES, PROCESSES FOR THE PREPARATION THEREOF, AND PHARMACEUTICAL COMPOSITIONS CONTAINING THEM

BACKGROUND OF THE INVENTION

Protein kinase C (PKC) plays a very important part in the regulation of cellular processes which are closely linked with the physiological control of contractile, secretory and proliferative processes (Y. Nishizuka, Nature, 308, 693–698/1984). The novel 2-acyloxypropylamine derivatives of the present invention are the first group of compounds which inhibit PKC and the thrombocyte aggregation stimulated by diacylglycerols.

SUMMARY OF THE INVENTION

The present invention is concerned with new 2-acyloxypropylamine derivatives, processes for the preparation thereof, pharmaceutical compositions containing them, and methods for using them.

DETAILED DESCRIPTION

The new 2-acyloxypropylamine derivatives of the present invention are compounds of formula

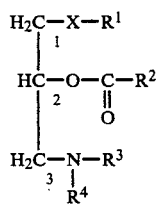

(I)

wherein $R^1$ is a straight-chained or branched, saturated or unsaturated alkyl radical containing up to 20 carbon atoms, $R^2$ is a straight-chained or branched alkyl radical containing up to 4 carbon atoms, $R^3$ and $R^4$, which can be the same or different, are hydrogen atoms, benzyl, or straight-chained or branched alkyl radicals containing up to 14 carbon atoms which are optionally phenylsubstituted or $R^3$ and $R^4$ together form a piperidine or piperazine ring each of which can be optionally substituted by alkyl radicals containing up to 4 carbon atoms and X is an oxygen or sulphur atom; and the pharmacologically acceptable salts thereof. Preferred derivatives of formula (I) are those in which $R^3$ and $R^4$ which can be the same or different are hydrogen, benzyl, or straight-chained or branched, substituted by phenyl or unsubstituted alkyl radical containing up to 14 carbon atoms.

Other preferred 2-acyloxypropylamine derivatives of formula (I) are those in which $R^1$ is a propyl, octadecyl, octadecenyl, tetradecyl, hexadecyl, eicosanoyl, or isobutyl alkyl radical, $R^2$ a methyl or isopropyl radical, $R^3$ and $R^4$ which may be the same or different and are hydrogen atoms or methyl, ethyl, propyl, or benzyl radicals, or together form a piperidine or 2-methylpiperazine ring, and X is an oxygen or sulfur atom.

Especially preferred compounds according to the present invention are:
(±)-3-dimethylamino-1-octadecyloxy-2-propyl acetate,
(±)-3-dibenzylamino-1-octadecyloxy-2-propyl acetate,
(±)-3-dimethylamino-1-propoxy-2-propyl propionate oxalate,
1-(2-methyl)-piperazinyl-3-octadecyloxy-2-propyl acetate oxalate,
(±)-3-dimethylamino-1-tetradecyloxy-2-propyl acetate,
(±)-3-dimethylamino-1-hexadecyloxy-2-propyl acetate,
(±)-3-dimethylamino-1-eicosanyloxy-2-propyl acetate,
(±)-3-di-n-butylamino-1-octadecyloxy-2-propyl acetate oxalate,
(±)-3-dimethylamino-1-octadecyloxy-2-propyl isobutyrate,
(±)-3-dimethylamino-1-isobutoxy-2-propyl acetate oxalate,
(±)-3-(N-benzyl-N-methyl)-amino-1-octadecyloxy-2-propyl acetate,
(±)-3-dimethylamino-1-(2-hexadecyloxy)-2-propyl acetate,
(±)-3-dimethylamino-1-(9-cis-octadeconyloxy)-2-propyl acetate,
(±)-3-amino-1-octadecyloxy-2-propyl acetate,
(±)-3-methylamino-1-octadecyloxy-2-propyl acetate, and
(±)-3-dimethylamino-1-octadecylthio-2-propyl acetate.

The present invention also provides a process for the preparation of 2-acyloxypropylamine derivatives of formula (I), wherein
(1.) a compound of formula (II)

(II)

in which Y is a group which can easily be removed, for example a tosyl radical or a halogen atom, is reacted with a compound of formula (III)

$$HX\text{-}R^1 \qquad (III)$$

in which $R^1$ and X have the above-given meanings, either
(a) if X is oxygen in an aqueous organic two-phase system to a compound of formula (IV)

(IV)

in which $R^1$ has the above meaning and X is oxygen, or
(b) if X is sulfur in an alcohol in the presence of a tertiary amine to a compound of formula VIII

(VIII)

in which $R^1$ and Y have the above meaning and X is sulfur, which is subsequently reacted with sodium alcoholate to a compound of general formula IV wherein X is sulfur,
(2.) reacting the obtained compounds of formula IV with an amine of formula (V)

in which $R^{3'}$ and $R^{4'}$ have the same meanings as above for $R^3$ and $R^4$ other than hydrogen, to give, with opening of the epoxide ring, a compound of formula (VI)

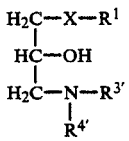

in which $R^1$, $R^{3'}$, $R^{4'}$ and X have the above meanings, and (3.) which are subsequently acylated in known manner to give the desired compounds of formula (I), which are (4.) finally if desired for the case that $R^3$ and/or $R^4$ are benzyl radicals reacted by catalytic hydrogenation to compounds of formula I in which $R^3$ and/or $R^4$ are hydrogen atoms.

The epoxides of formula (II), especially epichlorohydrin and epibromohydrin, are commercially available, as are the alcohols of formula (III) and the amines of formula (V).

The reaction of compounds of formula (II) to give ethers of formula (IV) can be carried out by processes known from the literature (Synthesis, 1983, 117) for alcohols up to a chain length of 10 carbon atoms. Longer chained alcohols can be reacted when the reaction is carried out in known manner in a substantially immiscible aqueous organic, strongly alkaline two-phase system, for example of dichloromethane and 50% aqueous sodium hydroxide solution in a ratio of from 10:1 to 3:1 and preferably of from 5-6:1 v/v. Furthermore, it is preferable to work at an elevated temperature, especially at the boiling point of the solvent. The reaction time is from 16 to 25 hours and preferably about 20 hours. The reaction products can be isolated and purified by known separation processes, for example crystallization and/or chromatography.

For the preparation of the aminoalcohols of formula (VI), the compounds of formula (IV) are reacted with appropriate amines of formula (V) in a protic solvent, preferably in water, with heating to a temperature of from 40° to 100° C. and preferably of from 60° to 80° C. Other solvents which can be used include lower alcohols, especially isopropanol, methanol or ethanol. The reaction time is from 1 to 5 hours and usually about 3 hours.

Thioethers of formula IV are prepared in known manner (Pol. J. Chem. 58, 1237, 1984) by reacting epoxides of formula II with mercaptans of formula III in a water-free alcohol like ethanol or isopropanol, preferred methanol, at temperatures between 20° and 100° C., preferred between 40° to 50° C., in the presence of a tertiary amine, preferred triethylamine, under opening of the oxirane ring to thioethers of formula VIII, which are subsequently reacted to compounds of formula IV with alcoholates like sodium ethylate or potassium t.-butylate, preferred sodium methylate, in the corresponding alcohol. The reaction products are isolated and purified by the known separating methods such as crystallization and/or chromatography.

The reaction of the aminoalcohols of formula (VI) to give the compounds of formula (I) according to the present invention takes place according to known processes either by a process in which, (Houben-Weyl, Vol. VIII, p. 547 et seq.), an equivalent or excess but preferably the double amount of an appropriate carboxylic acid anhydride is reacted in a tertiary amine, preferably in anhydrous pyridine, as adjuvant base and simultaneously as solvent with the aminoalcohol in question at a temperature of from 5° to 50° C. but preferably of about 25° C. for 15 to 30 hours and preferably for about 24 hours or, according to a process in which (Houben-Weyl, Vol. VIII, p. 543 et seq.) an equivalent amount of an appropriate carboxylic acid halide, especially of a carboxylic acid chloride, is reacted in an equivalent amount of a tertiary amine, preferably of triethylamine, in an inert solvent, such as dichloromethane, 1,1,2-trichloroethane or toluene, with the aminoalcohol in question at a temperature of from 5° to 50° C. but preferably of about 25° C. for 1 to 4 hours but preferably for about 2 hours. For both variants, the isolation and purification of the products can take place by chromatography and/or crystallization.

The optionally required catalytic hydrogenation of N-benzyl and of N,N-dibenzyl compounds of general formula (I) is carried out by dissolving the appropriate educts in a polar solvent, such as methanol or ethanol, and saturating with hydrogen, preferably at atmospheric pressure and ambient temperature in the presence of palladium on charcoal as catalyst. The products are obtained by crystallization of appropriate salts, preferably of the hydrochlorides.

Since the compounds according to the present invention of formula (I) can have a chiral center at C-2, they are present either as racemic mixtures or in the form of the enantiomers. The racemic mixtures can be resolved into individual enantiomers by known means.

Since the compounds of formula (I) have a basic center on C-3, for the purpose of purification or for galenical reasons, they can be converted with the help of inorganic or organic acids preferably into crystalline, pharmacologically acceptable salts. As acids, there can be used, for example, hydrochloric acid, sulphuric acid, phosphoric acid, hydrobromic acid, acetic acid, tartaric acid, lactic acid, citric acid, malic acid, salicylic acid, ascorbic acid, malonic acid, oxalic acid or succinic acid.

The compounds of formula (I) according to the present invention display interesting pharmacological properties. They are the first group of compounds which inhibit protein kinase C (PKC) and the thrombocyte aggregation stimulated by diacylglycerols, for example oleoylacetylglycerol.

It is well-known that protein kinase C plays a very important part in the regulation of cellular processes which are closely linked with the physiological control of contractile, secretory and proliferative processes (Y. Nishizuka, Nature, 308, 693-698/1984). The physiological activation of protein kinase C takes place via a "second messenger", the diacylglycerol, resulting by receptor-determined breakdown of membrane-bound phosphatidylinositols.

Accordingly, the compounds of the present invention can be used for the treatment of cardiovascular diseases, that is, heart and circulatory diseases, such as thromboses, arterioscleroses, hypertension, rheumatic inflammatory processes, allergies, cancers and certain degenerative damage of the central nervous system.

Thus, the present invention provides pharmaceutical compositions containing at least one of the new compounds according to the present invention in admixture with conventional adjuvants.

The following examples are given for the purpose of illustrating the present invention:

EXAMPLES

Example 1

(±)-3-Dimethylamino-1-octadecyloxy-2-propyl acetate hydrochloride.

A mixture of 2.7 g (7 mMole) (±)-3-dimethylamino-1-octadecyloxy-2-propanol and 2.2 g (21 mMole) acetic anhydride in 20 ml pyridine is stirred at ambient temperature for 24 hours. The solvent and excess acetic anhydride are distilled off in a vacuum and the residue is taken up in 150 ml diethyl ether. This is mixed with diethyl ether saturated with gaseous hydrogen chloride and the precipitate obtained is filtered off with suction, washed with diethyl ether, suspended in 100 ml diethyl ether and subsequently stirred for 1 hour. After filtering off with suction, there is obtained a colorless product; yield 70%; m.p. 74°–75° C., The (±)-3-dimethylamino-1-octadecyloxy-2-propanol used as precursor is prepared as follows:

5.1 g (16 mMole) 1-octadecyloxy-2,3-epoxypropane and 28 g of a 40% solution of dimethylamine in water are heated for 3 hours to 80° C., while stirring. The solution is cooled and the solid residue is separated off, washed with water and dissolved in 400 ml dichloromethane. After the addition of 100 ml 2N hydrochloric acid, the mixture is intensively stirred for 30 minutes, the organic phase is separated off, dried over anhydrous magnesium sulphate and the solvent removed in a vacuum. After taking up the residue in 200 ml n-pentane under reflux, the hot suspension is filtered hot and the residue, after dissolving in dichloromethane, is treated with 2N aqueous sodium hydroxide solution. After separating off the organic phase, drying it over anhydrous magnesium sulphate and distilling off the solvent in a vacuum, the product is isolated; m.p. 72°–82° C., The (±)-1-octadecyloxy-2,3-epoxypropane used as starting material is prepared as follows:

A mixture of 70 ml 50% aqueous sodium hydroxide solution, 46.2 g (0.5 mole) epichlorohydrin, 27.0 g (0.1 mole) octadecanol and 1.7 g tetrabutylammonium hydrogen sulphate in 400 ml dichloromethane is intensively stirred for 16 hours at 40° C., After the addition of a further 1.0 g of catalyst, stirring is continued for 4 hours at this temperature. The reaction solution is then cooled, the organic phase is separated off, washed with water, dried over anhydrous magnesium sulphate and freed from solvent in a vacuum. The remaining epichlorohydrin is distilled off and the residue separated by column chromatography (silica gel; dichloromethane/cyclohexane; 2:1 v/v). The colorless product obtained has a melting point of 74°–75° C., The following compounds were obtained in an analogous manner:

1 a) (±)-1-octadecyloxy-3-piperidino-2-propyl acetate hydrochloride; m.p. 105°–106° C. (recrystallized from diethyl ether); yield 69.6%;

1 b) (±)-3-dibenzylamino-1-octadecyloxy-2-propyl acetate hydrochloride; m.p. >64° C. (recrystallized from n-pentane); yield 68%;

1 c) (±)-3-dimethylamino-1-propoxy-2-propyl propionate oxalate; m.p. 110°–115° C. (recrystallized from diethyl ether); yield 62.5%;

1 d) 1-(2-methyl)-piperazinyl-3-octadecyloxy-2-propyl acetate oxalate; m.p. >75° C. (recrystallized from ethanol); yield 70%;

1 e) (±)-3-dimethylamino-1-tetradecyloxy-2-propyl acetate hydrochloride; m.p. 61°–65° C. (recrystallized from n-pentane); yield 93.8%;

1 f) (±)-3-dimethylamino-1-hexadecyloxy-2-propyl acetate hydrochloride; m.p. 48°–52° C. from n-pentane; yield 71%;

1 g) (±)-3-dimethylamino-1-eicosanyloxy-2-propyl acetate hydrochloride; m.p. >77° C. from ether; yield 98%;

1 h) (±)-3-di-n-butylamino-1-octadecyloxy-2-propyl acetate oxalate; m.p. 70°–78° C. from n-pentane; yield 18.7%;

1 i) (±)-3-dimethylamino-1-octadecyloxy-2-propyl isobutyrate hydrochloride; m.p. 92°–94° C. from n-pentane; yield 56.2%;

1 j) (±)-3-dimethylamino-1-isobutoxy-2-propyl acetate oxalate; m.p. 126°–131° C. from ethylacetate/acetone; yield 32.5%;

1 k) (±)-3-(N-benzyl-N-methyl)-amino-1-octadecyloxy-2-propyl acetate hydrochloride; m.p. 81°–86° C. from n-pentane; yield 76.6%;

1 l) (±)-3-dimethylamino-1-(2-hexadecyloxy)-2-propyl acetate hydrochloride; m.p. 78°–89° C. from n-pentane; yield 83.6%; and 1 m) (±)-3-dimethylamino-1-(9-cis-octadecenyloxy)-2-propyl acetate hydrochloride; yield 90.5%; $^1$H-NMR (CDCl$_3$): 5.25–5.4 (2H,m), 5.05–5.15 (1H,m), 3.35–3.6 (4H,m), 2.4–2.6 (2H,m), 2.25 (6H,s), 2.05 (3H,s), 1.9–2.15 (4H,m), 1.4–1.65 (3H,m), 1.15–1.4 (21H,m), 0.90 (3H,t).

EXAMPLE 2

(±)-3-Amino-1-octadecyloxy-2-propyl acetate hydrochloride 1.5 g (2.5 mMole) (±)-3-dibenzylamino-1-octadecyloxy-2-propyl acetate hydrochloride (Example 1 b) is dissolved in 30 ml ethanol and reacted with hydrogen up to saturation at atmospheric pressure and ambient temperature in the presence of 0.3 g palladium/charcoal as catalyst. The reaction mixture is subsequently filtered, the solvent is distilled off in a vacuum and the residue is taken up in 40 ml diethyl ether. With stirring, the product separates out in solid form; m.p. 62° C.; yield 95%.

The following compound was obtained in an analogous manner:

2 a) (±)-3-methylamino-1-octadecyloxy-2-propyl acetate hydrochloride; m.p. 109°–113° C. from n-hexane; yield 61%.

EXAMPLE 3

(±)-3-Dimethylamino-1-octadecylthio-2-propyl acetate hydrochloride 1.3 g (3.4 mMole) (±)-3-dimethylamino-1-octadecylthio-2-propanol is dissolved with 0.7 g (6.7 mMole) acetic anhydride in 30 ml water-free pyridine and stirred at ambient temperature for 18 hours. The solvent is distilled off in a vacuum, the residue is taken up in 20 ml n-hexane, and cooled to −20° C. to yield 200 mg of the educt by crystallization. The educt is filtered off, the solvent is distilled off in a vacuum from the mother liquor, and the residue is dissolved in 60 ml ether. A saturated hydrochloric acid ether solution is added while stirring until the solution is acidic. The hydrochloride of the product separated out in solid form is filtered off, washed with ether, and dried in a vacuum. The colorless product yielding 88.2% with m.p. 76°–80° C., The (±)-3-dimethylamino-1-octadecylthio-2-propanol used as precursor is prepared as follows:

1.2 g (3.5 mMole) 1-octadecylthio-2,3-epoxypropane and 2.0 g (17.5 mMole) of a 40% solution of dimethylamine in water are heated for 4 hours to 80° C., while stirring. The solution is cooled and after adding of 100 ml dichloromethane and 100 ml water the organic phase is separated off, dried over sodium sulphate and the solvent removed in a vacuum. After taking up the residue in 30 ml ether and cooling to −20° C. the precipitate is separated and after distilling off the solvent from the mother liquor the product is obtained as oil which solidifies at ambient temperature.

The (±)-1-octadecylthio-2,3-epoxypropane used as precursor is prepared as follows:

To a suspension of 0.58 g (18.5 mMole) sodium hydride (80% in paraffin oil) in 20 ml water-free tetrahydrofuran are added dropwise in a nitrogen atmosphere 20 ml of water-free methanol, while cooling with water. To the clear solution then a solution of 7.0 (18.5 mMole) (±)-3-chloro-1-octadecylthio-2-propanole in 30 ml of water-free methanol is added and the solution is stirred for 1 hour at ambient temperature. The reaction solution is then freed from solvent in a vacuum and the residue is taken up in 200 ml dichloromethane. The organic phase is separated off, washed with 50 ml water, dried over sodium sulphate and the solvent is distilled off in a vacuum from the colorless product with a m.p. >33° C.

The (±)-3-chloro-1-octadecylthio-2-propanol used as starting material is prepared as follows:

A mixture of 14.3 g (50 mMole) octadecylmercaptane, 4.6 g (50 mMole) epichlorohydrine and 5.1 g (50 mMole) triethylamine in 100 ml water-free methanol is stirred for 2 hours at 45° C., After cooling to ambient temperature and the mucous precipitate is separated, washed with methanol and purified chromatographically on silica gel with ether/chclohexane (1:3; v/v). With the third fraction the product is separated with m.p. >45° C.

COMPARATIVE EXPERIMENTS

The following comparative experiments illustrate the pharmacological effectiveness of the compounds according to the present invention of formula (I):

1. Inhibition of the enzyme protein kinase C.

For the elucidation of the inhibiting influence of the compounds according to the present invention of general formula (I) on the calcium- and phospholipid-dependent protein kinase (PKC), this enzyme activity was enriched, starting from a chicken gizzard extract. The two-step procedure according to purification steps described in the literature (J. Biol. Chem., 260, 15718–15722/1985) utilized the property of the enzyme of binding in the presence of calcium to cell membranes and again dissolving off by calcium chelators (EGTA). In the first purification step, there took place the binding of the PKC to membranes of the chicken gizzard extract and, in the second step, to the so-called inside out vesicles of erythrocytes. After dissolving from the erythrocyte membranes and rebuffering, the PKC preparation was present in 10 mM HEPES, 1 mM DTT and 0.1% PEG 20,000 (pH 7.5) and, under these conditions, it could be stored for several months at −70° C. without loss of activity.

The activity of the enzyme was determined via the incorporation of phosphorus 32-labelled phosphate into the protein histon H-1, which is phosphorylatable by PKC. The test thereby contained the following components: 50 mM HEPES (pH 7.5), 1 mM DTT, 5 mM magnesium chloride, about 10 μM free calcium ions, 200 μg/ml histone, 5 μg/ml phosphatidylserine, 1 μg/ml 1,2-diolein, 10 μuM ATP, in each case an appropriate amount of PKC preparation and optionally a test substance. The kinase activity measured under standard conditions in the presence of PKC activators (and without test substance) was, in each case, taken as being 100% and the inhibitory action of the compounds of general formula (I) referred thereto as a percentage.

The results thus obtained are set out in the following Table 1:

TABLE 1

Inhibition of PS/DO-mediated PKC activity and of OAG-induced platelet aggregation

| Compound of Example | Concen. (mol/l) | Inhibition of PS/DO-Mediated PKC-Activity (%) | Inhibition of OAG-Induced Platelet Aggregation (mol/l) |
|---|---|---|---|
| 1 | $10^{-4}$ | 86 | 100 |
| 1 | $10^{-5}$ | 61 | 48 |
| 1 | $10^{-6}$ | 24 | 2 |
| 1.a | $10^{-4}$ | 25 | 54 |
| 1.b | $10^{-5}$ | 22 | |
| 1.c | $10^{-4}$ | 9 | |
| 1.d | $10^{-5}$ | 61 | 100 |
| 1.d | $3 \times 10^{-6}$ | | 14 |
| 1.d | $10^{-6}$ | 18 | 0 |
| 1.e | $10^{-5}$ | 14 | |
| 1.f | $10^{-5}$ | 27 | |
| 1.g | $10^{-5}$ | 39 | 53 |
| 1.l | $10^{-5}$ | 31 | |
| 1.m | $10^{-5}$ | 48 | |
| 1.m | $10^{-6}$ | 14 | |
| 2 | $10^{-4}$ | 44 | |
| 2 | $10^{-5}$ | 18 | |
| 2.a | $10^{-5}$ | 35 | |
| 2.a | $10^{-6}$ | 13 | |
| 3 | $10^{-4}$ | 70 | |
| 3 | $10^{-5}$ | 22 | |

PS = phosphatidylserine
DO = 1,2-dioleine
OAG = oleoylacetylglycerol

2. Influence of the compound of Example 1 on platelet aggregation stimulated by oleoylacetylglycerol.

For carrying out the aggregation experiments, use was made of gel-filtered human thrombocytes. These were prepared in the following way: after centrifuging human blood for 15 minutes at 60 xg, the supernatant, i.e., the platelet-rich plasma, was used for the gel filtration. By means of the gel filtration through a column packed with Sepharose CL-2B, the platelets were transferred into a calcium-free, defined buffer medium (15 mM tris, 150 mM sodium chloride, 5.5 mM glucose, 0.2% bovine serum albumin; pH 7.4). Subsequently, the platelets were recalcified to a concentration of $7 \times 10^{-4}$M calcium. The platelets were then incubated at 37° C. in an aggregometer and, after initiation of the aggregation by a stimulus, the decrease of the absorption was determined as a measure of the aggregation. As aggregation-initiating stimulus, there was used 1-oleoyl-2-acetylglycerol (OAG), an activator of the enzyme protein kinase C (J. Biol. Chem., 258, 6701-6704/1983) in a concentration of $5 \times 10^{-5}$M. The aggregation achieved under these conditions was taken as being 100% control. The carrying out of the experiments on the influence of the compound of Example 1 on the OAG-stimulated aggregation took place in the following way: the platelets were first incubated for 3 minutes with the compound of Example 1 at the given concentration and subsequently the aggregation was initiated with OAG. The reduced extent of the aggregation was, in each case, calculated as a percentage of the 100% control. The results obtained are set out in Table 1 as well.

We claim:

1. A compound of the formula

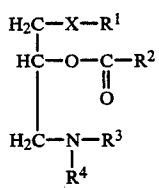 (I)

wherein $R^1$ is propyl, octadecyl, octadecenyl, tetradecyl, hexadecyl, eicosanyl, or isobutyl; $R^2$ is methyl or isopropyl and $R^3$ and $R^4$ may be the same or different and are hydrogen, methyl, propyl, or benzyl.

2. A compound named (±)-3-dimethylamino-1-octadecyloxy-2-propyl acetate.

3. A compound named (±)-3-dibenyzlamino-1-octadecyloxy-2-propyl acetate.

4. A compound named (±)-3-dimethylamino-1-propoxy-2-propyl propionate oxalate.

5. A compound named 1-(2-methyl)-piperazinyl-3-octadecyloxy-2-propyl acetate oxalate.

6. A compound named (±)-3-dimethylamino-1-tetradecyloxy-2-propyl acetate.

7. A compound named (±)-3-dimethylamino-1-hexadecyloxy-2-propyl acetate.

8. A compound named (±)-3-dimethylamino-1-eicosanyloxy-2-propyl acetate.

9. A compound named (±)-3-di-n-butylamino-1-octadecyloxy-2-propyl acetate oxalate.

10. A compound named (±)-3-dimethylamino-1-octadecyloxy-2-propyl isobutyrate.

11. A compound named (±)-3-dimethylamino-1-isobutoxy-2-propyl acetate oxalate.

12. A compound named (±)-3-(N-benzyl-N-methyl)-amino-1-octadecyloxy-2-propyl acetate.

13. A compound named (±)-3-dimethylamino-1-(2-hexadecyloxy)-2-propyl acetate.

14. A compound named (±)-3-dimethylamino-1-(9-cisoctadecenyloxy)-2-propyl acetate.

15. A compound named (±)-3-amino-1-octadecyloxy)-2-propyl acetate.

16. A compound named (±)-3-methylamino-1-octadecyloxy)-2-propyl acetate.

17. A compound named (±)-3-dimethylamino-1-octadecythio-2-propyl acetate.

18. A pharmaceutical composition comprising a protein kinase C inhibiting amount of a compound according to claim 3 together with a pharmaceutically acceptable carrier.

19. A method for inhibiting protein kinase C in mammals which comprises administering to said mammal a pharmaceutical composition according to claim 18.

20. A method of inhibiting thrombocyte aggregation in mammals which comprises administering to said mammal a pharmaceutical composition according to claim 18.

21. A method of treating cardiovascular diseases in mammals which comprises administering to said mammal a pharmaceutical composition according to claim 18.

* * * * *

UNITED STATES PATENT AND TRADEMARK OFFICE
CERTIFICATE OF CORRECTION

PATENT NO. : 4,855,489
DATED : August 8, 1989
INVENTOR(S) : Trostmann et al.

It is certified that error appears in the above—identified patent and that said Letters Patent is hereby corrected as shown below:

Column 10, line 16 delete "cisoctadecenyloxy)" and insert -- cis-octadecenyloxy) --

Signed and Sealed this

Tenth Day of July, 1990

Attest:

HARRY F. MANBECK, JR.

Attesting Officer

Commissioner of Patents and Trademarks